(12) United States Patent
Thornes et al.

(10) Patent No.: US 8,911,446 B2
(45) Date of Patent: Dec. 16, 2014

(54) ALIGNMENT JIG FOR A BONE FIXATION DEVICE

(75) Inventors: Brian Thornes, Malahide (IE); Ross McDonald, Bailey Howth (IE)

(73) Assignee: Sota Orthopaedics Limited, Dublin (IE)

(*) Notice: Subject to any disclaimer, the term of this patent is extended or adjusted under 35 U.S.C. 154(b) by 205 days.

(21) Appl. No.: 13/177,411

(22) Filed: Jul. 6, 2011

(65) Prior Publication Data

US 2013/0012948 A1  Jan. 10, 2013

(51) Int. Cl.
*A61B 17/58* (2006.01)
*A61B 17/60* (2006.01)
*A61F 2/00* (2006.01)
*A61B 17/17* (2006.01)

(52) U.S. Cl.
CPC ......... *A61B 17/1725* (2013.01); *A61B 17/1703* (2013.01)
USPC .............................................. 606/96; 606/104

(58) Field of Classification Search
USPC .................. 606/62–68, 86 R, 87, 96–99, 104
See application file for complete search history.

(56) References Cited

U.S. PATENT DOCUMENTS

| 6,183,477 B1* | 2/2001 | Pepper .......................... 606/104 |
| 7,488,328 B2* | 2/2009 | Gotfried .......................... 606/99 |
| 8,241,286 B2* | 8/2012 | Metzinger et al. .............. 606/62 |
| 2012/0053641 A1* | 3/2012 | Meridew .................... 606/86 R |

* cited by examiner

*Primary Examiner* — Andrew Yang
*Assistant Examiner* — Diana S Jones
(74) *Attorney, Agent, or Firm* — Stites & Harbison PLLC; Richard S. Myers, Jr.

(57) ABSTRACT

A jig for a bone fixation device, including those that comprise a guide; and a connecting element reversibly engagable with the bone fixation device; wherein the guide defines a non-rectilinear path and is adapted to receive the connecting element; and wherein the connecting element is remotely operable, and is adapted to permit a tool to be engaged with the bone fixation device. Other embodiments of the present invention include methods for placing a bone fixation device in a bone, using a jig of the present invention comprising the step of reversibly engaging the bone fixation device with the jig.

18 Claims, 8 Drawing Sheets

ALIGNMENT JIG FOR A BONE FIXATION DEVICE

FIELD OF THE INVENTION

This invention generally relates to a jig for a bone fixation device, in particular an alignment jig for the placement of a bone fixation device. Specifically, embodiments of the include a jig comprising a guide, and a connecting element for reversibly engaging the bone fixation device.

BACKGROUND TO THE INVENTION

Bone fixation devices are well known and they find particular utility in the field of orthopaedic surgery, where they are used to fix a bone, which has sustained a fracture, across the fracture site.

The use of bone fixation devices, such as intramedullary nails, allows the fixing of a bone, without the need to surgically expose the fracture site of the bone, thus permitting minimally invasive surgery. An alignment jig connected to the intramedullary nail facilitates the targeted placement of transfixing screws or bolts with respect to the intramedullary nail.

In use, bone fixation devices, such as intramedullary nails, are connected to an alignment jig to facilitate targeted placement. Commonly, the alignment jig is connected to the bone fixation device by a threaded connecting bolt, the threaded portion of which engages with the bone fixation device and is securely, but reversibly, connected to the bone fixation device.

In use, an alignment jig is connected to the bone fixation device at the distal end of the alignment jig, usually close to and in line with the connecting end of the bone fixation device; whereas an operator, for example an orthopaedic surgeon, is located at the proximal end of the alignment jig. A wrench or spanner is usually used to connect or disconnect the alignment jig and the bone fixation device; wherein the wrench or spanner has to be skillfully guided deep into the surgical field in order to be used.

In certain situations of use, such as in large or obese patients, and in the region of the proximal femur, the interface between the distal end of the alignment jig and the bone fixation device may be located deep within the surgical field, within the patient.

Moreover, with respect to certain bone fixation devices, there is a need to operate a subcomponent of the bone fixation device at the connecting end of the device (at the distal end of the alignment jig), for example, axially advancing or retracting a setscrew for locking a transfixion bolt. Such operation may also involve the skilful freehand insertion of an instrument or tool deep into the surgical wound in order to reach the subcomponent of the bone fixation device.

SUMMARY OF THE INVENTION

According to a first aspect of the present invention, there is provided a jig for a bone fixation device, the jig comprising a guide; and a connecting element reversibly engagable with the bone fixation device; wherein the guide defines a non-rectilinear path and is adapted to receive the connecting element; and wherein the connecting element is remotely operable, and is adapted to permit a tool to be engaged with the bone fixation device.

Optionally, the bone fixation device is a bone fixation rod (or nail). Further optionally, the bone fixation device is an intramedullary rod (or intramedullary nail).

Optionally, the guide is adapted to allow the passage of the connecting element therethrough.

Optionally, the guide has a hollow body having open ends. Further optionally, the guide has a hollow cylindrical body having open ends.

Optionally or additionally, the guide has first and second open ends. Further optionally or additionally, the guide has a hollow cylindrical body, and first and second open ends.

Optionally, at least part of the guide defines a curvilinear path.

Optionally, the ends of the guide do not share the same rectilinear axis. Further optionally, at least part of the guide defines a curvilinear path, such that the first and second ends of the guide do not share the same rectilinear axis.

Optionally, the first end of the guide is in non-parallel orientation with respect to the second end of the guide.

Optionally, the connecting element is, in use, located adjacent a first end of the guide. Further optionally, the connecting element is, in use, located at a first end of the guide.

Optionally, the connecting element is arranged for movement relative to the guide. Further optionally, the connecting element is arranged for rotational movement relative to the guide, optionally about a longitudinal axis of the guide. Still further optionally, the connecting element is arranged for rotational movement about a longitudinal axis of the first end of the guide.

Optionally, the connecting element is arranged for co-axial rotation within the guide.

Optionally, the connecting element has a hollow body having open ends. Further optionally, the connecting element has a hollow cylindrical body having open ends.

Optionally, the connecting element has first and second open ends. Further optionally, the connecting element has a hollow cylindrical body, and first and second open ends.

Optionally, the connecting element has a hollow cylindrical body, and first and second open ends.

Optionally, the connecting element is adapted to reversibly engage the bone fixation device. Further optionally, the connecting element is shaped and dimensioned to reversibly engage the bone fixation device.

Optionally, in use, the connecting element is co-terminally engaged with the bone fixation device. Further optionally, in use, the connecting element is reversibly co-terminally engaged with the bone fixation device.

Optionally or additionally, the connecting element is shaped and dimensioned to form an interference fit with the bone fixation device. Further optionally or additionally, the connecting element comprises a lip, which is shaped and dimensioned to form an interference fit with the bone fixation device.

Optionally or additionally, the connecting element is adapted for threaded engagement with the bone fixation device. Further optionally, the connecting element comprises a screw thread for threaded engagement with a corresponding screw thread of the bone fixation device. Still further optionally, the connecting element comprises a screw thread at a bone fixation device-engaging face, and the bone fixation device comprises a corresponding screw thread at a connecting element-engaging face.

Optionally, the connecting element is adapted to allow the passage of a tool therethrough. Further optionally, the connecting element comprises an aperture to allow the passage of a tool therethrough.

Optionally, the connecting element is integral with the guide. Alternatively, the connecting element is separate from the guide.

Optionally, the connecting element is separate from the guide, and the guide is adapted to receive the connecting element. Further optionally, the guide is adapted to receive the connecting element at the second end of the guide and to allow the passage of the connecting element therethrough. Still further optionally, the guide comprises a stop to reversibly retain the connecting element adjacent or at the first end of the guide.

Optionally, the stop is adapted to reversibly retain the connecting element at the first end of the guide, but to allow the passage of a tool therethrough. Further optionally, the stop is shaped and dimensioned to reversibly retain the connecting element at the first end of the guide, but to permit the passage of a tool therethrough. Still further optionally, the stop comprises a projection, which projects radially inward with respect to the first end of the guide to reversibly retain the connecting element at the first end of the guide.

Optionally, the projection defines an aperture, which permits the passage of a tool therethrough Optionally, the connecting element comprises an actuator.

Optionally, the actuator is arranged for rotational motion relative to the guide, optionally about a longitudinal axis of the guide.

Optionally, the actuator is integral with the connecting means. Alternatively, the actuator is separate from the connecting means.

Optionally, the actuator is adapted to reversibly engage the connecting element. Further optionally, the actuator is shaped and dimensioned to reversibly engage the connecting element.

Optionally, the actuator comprises a hollow body, which extends between the first and second ends of the guide. Further optionally, the actuator comprises a hollow cylindrical body, which extends between the first and second ends of the guide.

Optionally, the actuator comprises a hollow cylindrical body, which is, in use, co-axial with, and extends between the first and second ends of, the guide.

Optionally, the actuator is arranged for co-axial rotation within the guide.

Optionally, the actuator is arranged to permit rotation of the connecting means relative to the guide. Further optionally, the actuator is arranged to permit rotation of the connecting means at the first end of the guide, optionally about a longitudinal axis of the guide.

Optionally, the actuator is arranged to permit rotation of the connecting means by rotation of the actuator. Further optionally, the actuator is arranged to permit rotation of the connecting means at the first end of the guide by rotation of the actuator at the second end of the guide.

Optionally, the actuator is arranged to translate rotational motion of the actuator to rotational motion of the connecting means. Further optionally, the actuator is arranged to translate rotational motion of the actuator at the second end of the guide to rotational motion of the connecting means at the first end of the guide.

Optionally, the actuator is arranged to translate rotational motion of the actuator in a first plane to rotational motion of the connecting means in a second plane, wherein the first and second planes are non-parallel planes. Further optionally, the actuator is arranged to translate rotational motion of the actuator at the second end of the guide to rotational motion of the connecting means at the first end of the guide.

Optionally, the actuator is formed from a resilient material. Further optionally, the actuator comprises a hollow body, which extends between the first and second ends of the guide and is formed from a resilient material. Still further optionally, the actuator comprises a hollow cylindrical body, which extends between the first and second ends of the guide and is formed from a resilient material.

Optionally, the actuator is formed from a flexible material. Further optionally, the actuator comprises a hollow cylindrical body, which extends between the first and second ends of the guide and is formed from a flexible material.

Alternatively, the actuator comprises a hollow cylindrical body having first and second ends. Optionally, the actuator comprises a hollow flexible cylindrical body having first and second ends.

Optionally, the actuator comprises at least two segments.

Optionally, the actuator comprises at least two segments, which are each arranged for reciprocal movement relative to the other segment. Further optionally, the actuator comprises at least two segments, which are each arranged for reciprocal movement relative to the other segment with respect to the longitudinal axis of the actuator.

Optionally, each segment of the actuator is arranged for displacement relative to an adjacent segment of the actuator. Further optionally, each segment of the actuator is arranged for reversible displacement relative to an adjacent segment of the actuator. Still further optionally, each segment of the actuator is arranged for reversible displacement relative to an adjacent segment of the actuator with respect to the longitudinal axis of the actuator.

Preferably, at least part of each segment of the actuator is arranged for reversible displacement relative to an adjacent segment of the actuator with respect to the longitudinal axis of the actuator. Further preferably, at least part of each segment of the actuator is arranged for reversible displacement relative to an adjacent segment of the actuator with respect to the longitudinal axis of the actuator, such that at least part of the actuator is axially deformed.

Optionally, at least part of each segment is connected to at least part of an adjacent segment. Further optionally, each pair of adjacent segments forms a corrugation defining an intermediate space between each of the segments. Optionally, at least part of each adjacent segment can be displaced relative to an adjacent segment by altering the intermediate space between each pair of segments.

Alternatively, each segment is spaced apart relative to an adjacent segment. Optionally, each segment is arranged for reversible displacement relative to an adjacent segment of the actuator with respect to the longitudinal axis of the actuator. Further optionally, each segment is arranged for limited reversible displacement relative to an adjacent segment of the actuator with respect to the longitudinal axis of the actuator.

Optionally, each segment is crenulated and comprises crenels arranged to receive crenels of an adjacent segment. Further optionally, the crenels of each segment are arranged for reversible displacement relative to the crenels of an adjacent segment of the actuator with respect to the longitudinal axis of the actuator. Further optionally, the crenels of each segment are arranged for limited reversible displacement relative to the crenels of an adjacent segment of the actuator with respect to the longitudinal axis of the actuator.

Preferably, the tip of each crenel has a greater dimension relative to the root of each crenel. Preferably, the tip of each crenel of each segment is shaped and dimensioned to, in use, engage with the base of each crenel of an adjacent segment.

Alternatively, at least one segment is formed from a deformable material. Optionally, at least one segment of each pair of adjacent segments is formed from a deformable material. Further optionally, at least one segment of each pair of adjacent segments is formed from a deformable material, such that at least part of the actuator is axially deformed.

Alternatively, the actuator is in the form of a helix or coil.

Preferably, the actuator is capable of rotational movement relative to the guide in a first direction. Optionally or additionally, the actuator is capable of rotational movement relative to the guide in a second direction. Further optionally, the actuator is capable of rotational movement relative to the guide in first and second opposing directions.

Optionally, in use, the guide and the actuator are co-axial and capable of rotational movement relative to one another.

Optionally, the actuator is adapted to allow the passage of a tool therethrough.

Optionally, the actuator is arranged for co-axial rotation of the tool therewithin.

Optionally, the tool is capable of exerting rotational motion. Further optionally, the tool has a flexible shaft. Still further optionally, the tool is a screwdriver having a flexible drive shaft.

Optionally, in use, the guide, the actuator, and the tool are co-axial and capable of independent rotational movement relative to one another.

Optionally, the jig further comprises at least one drill guide.

Optionally, the at least one drill guide is adapted to permit the passage of a drill bit therethrough.

Optionally, the bone fixation device comprises at least one drill guide.

Optionally, the at least one drill guide is adapted to permit the passage of a drill bit therethrough.

Optionally, the at least one drill guide of the jig and the at least one drill guide of the bone fixation device are, in use, co-axially oriented. Further optionally, the at least one drill guide of the jig and the at least one drill guide of the bone fixation device, in use, share the same longitudinal axis.

Optionally, each drill guide of the jig and each respective drill guide of the bone fixation device are, in use, co-axially oriented. Further optionally, each drill guide of the jig and each respective drill guide of the bone fixation device, in use, share the same longitudinal axis.

Optionally, the bone fixation device further comprises a device to fix a fracture in the bone. Further optionally, the bone fixation rod (or nail) further comprises a device to fix a fracture in the bone. Still further optionally, the intramedullary rod (or intramedullary nail) further comprises a device to fix a fracture in the bone.

Optionally, the fracture-fixing device extends across and fixes the fracture in the bone.

Optionally, the fracture-fixing device is a bone screw.

Optionally, the bone fixation device is adapted to be reversibly engagable with the fracture-fixing device.

Optionally, the bone fixation device comprises a screw for reversible engagement with the fracture-fixing device.

Optionally, the screw for reversible engagement with the fracture-fixing device is located, in use, adjacent the at least one drill guide of the bone fixation device. Still further optionally, the screw for reversible engagement with the fracture-fixing device is located, in use, adjacent the drill guide of the bone fixation device and is oriented, in use, to reversibly engage with the tool.

Optionally, the jig is formed from a sterilizable material. Further optionally, the jig is formed from an autoclavable material. Still further optionally, the jig is formed of a material that is suitable for sterilisation, so as to be provided in a sterile packaged state for use.

Optionally, the material is a plastic material, but it will be seen that any material that is suitable for sterilisation and can impart the required mechanical strength may be used. Further optionally, the material is a thermosetting plastic material.

Optionally, the material is polyether ether ketone (PEEK). Further optionally, the material is polyether ether ketone (PEEK), which is reinforced with fibres. Still further optionally, the material is polyether ether ketone (PEEK), which is reinforced with carbon fibres.

Alternatively, the material is stainless steel.

For the purposes of the present specification, a user or operator is a person who will undertake the operation of the device during routine use. Usually, this will be a medical professional, for example an orthopaedic surgeon, where routine use includes fixation of a bone of a patient. When in use, the invention is oriented so as to have a proximal end and a distal end relative to said user or operator.

A patient is defined as a person on whom the device will be used during routine operation.

According to a second aspect of the present invention, there is provided a method for placing a bone fixation device in a bone, using a jig according to the first aspect of the present invention, the method comprising the step of reversibly engaging the bone fixation device with the jig.

Optionally, the engaging step comprises engaging the connecting means of the jig to the bone fixation device.

Optionally, the engaging step further comprises rotating the connecting means relative to the guide.

Optionally, the engaging step further comprises rotating the connecting means by rotating the actuator. Further optionally, the engaging step further comprises rotating the connecting means at the first end of the guide by rotating the actuator at the second end of the guide.

Optionally, the engaging step comprises passing the actuator through the guide such that the guide and the actuator are co-axial and capable of rotational movement relative to one another.

Optionally, the method further comprises the step of introducing the bone fixation device into the bone. Further optionally, the method further comprises the step of introducing the bone fixation device into the medullary cavity of the bone. Still further optionally, the method further comprises the step of introducing the bone fixation device into, and longitudinally co-axial with, the medullary cavity of the bone.

Optionally, the method further comprises providing a channel into the medullary cavity of the bone prior to the introducing step. Further optionally, the method further comprises providing a channel into, and longitudinally co-axial with, the medullary cavity of the bone prior to the introducing step.

Optionally, the method further comprises the step of fixing a fracture in the bone.

Optionally, the fixing step comprises providing a channel across the fracture in the bone.

Optionally, the fixing step further comprises providing a channel extending between the at least one drill guide of the jig and the respective at least one drill guide of the bone fixation device.

Optionally, the fixing step further comprises introducing a fracture-fixing device across the fracture in the bone. Further optionally, the fixing step further comprises introducing a fracture-fixing device into the channel extending between the at least one drill guide of the jig and the respective at least one drill guide of the bone fixation device.

Optionally, the fixing step further comprises engaging the fracture-fixing device with the bone fixation device. Further optionally, the fixing step further comprises engaging the fracture-fixing device with the bone fixation device using a tool. Still further optionally, the fixing step further comprises engaging the fracture-fixing device with the bone fixation device by rotating a screw located, in use, adjacent the drill guide of the bone fixation device using the tool.

Optionally, the fixing step comprises passing the tool through the actuator such that the tool and the actuator are co-axial and capable of rotational movement relative to one another.

Further optionally, the fixing step comprises passing the tool through the actuator such that the tool and the actuator and the guide are co-axial and capable of independent rotational movement relative to one another.

Optionally, the method further comprises disengaging the connecting means of the jig from the bone fixation device.

Optionally, the disengaging step comprises rotating the connecting means relative to the guide.

Optionally, the disengaging step comprises rotating the connecting means by rotating the actuator. Further optionally, the disengaging step comprises rotating the connecting means at the first end of the guide by rotating the actuator at the second end of the guide.

Optionally, the method further comprises the step of reducing the fracture, prior to the providing step. Further optionally, the method further comprises the step of reducing the fracture by closed methods. Still further optionally, the method further comprises the step of reducing the fracture without surgical exposure of the fracture. Alternatively, the method further comprises the step of reducing the fracture by percutaneous methods. Optionally, the method further comprises the step of reducing the fracture with partial surgical exposure of the fracture. Further alternatively, the method further comprises the step of reducing the fracture by open methods. Optionally, the method further comprises the step of reducing the fracture with surgical exposure of the fracture.

Optionally, the method is conducted in connection with fluoroscopic techniques. Further optionally, the method is conducted in connection with image-intensifier fluoroscopic techniques. Still further optionally, the method is conducted in connection with x-ray image-intensifier fluoroscopic techniques. Alternatively, the method is conducted in connection with gamma-ray image-intensifier fluoroscopic techniques.

Optionally, the method is conducted on a patient, wherein the patient is oriented in the supine position. Alternatively, the method is conducted on a patient, wherein the patient is oriented in the lateral decubitous position.

BRIEF DESCRIPTION OF THE DRAWINGS

Embodiments of the present invention will now be described, with reference to the accompanying drawings in which.

DESCRIPTION OF THE INVENTION

Figure 1:
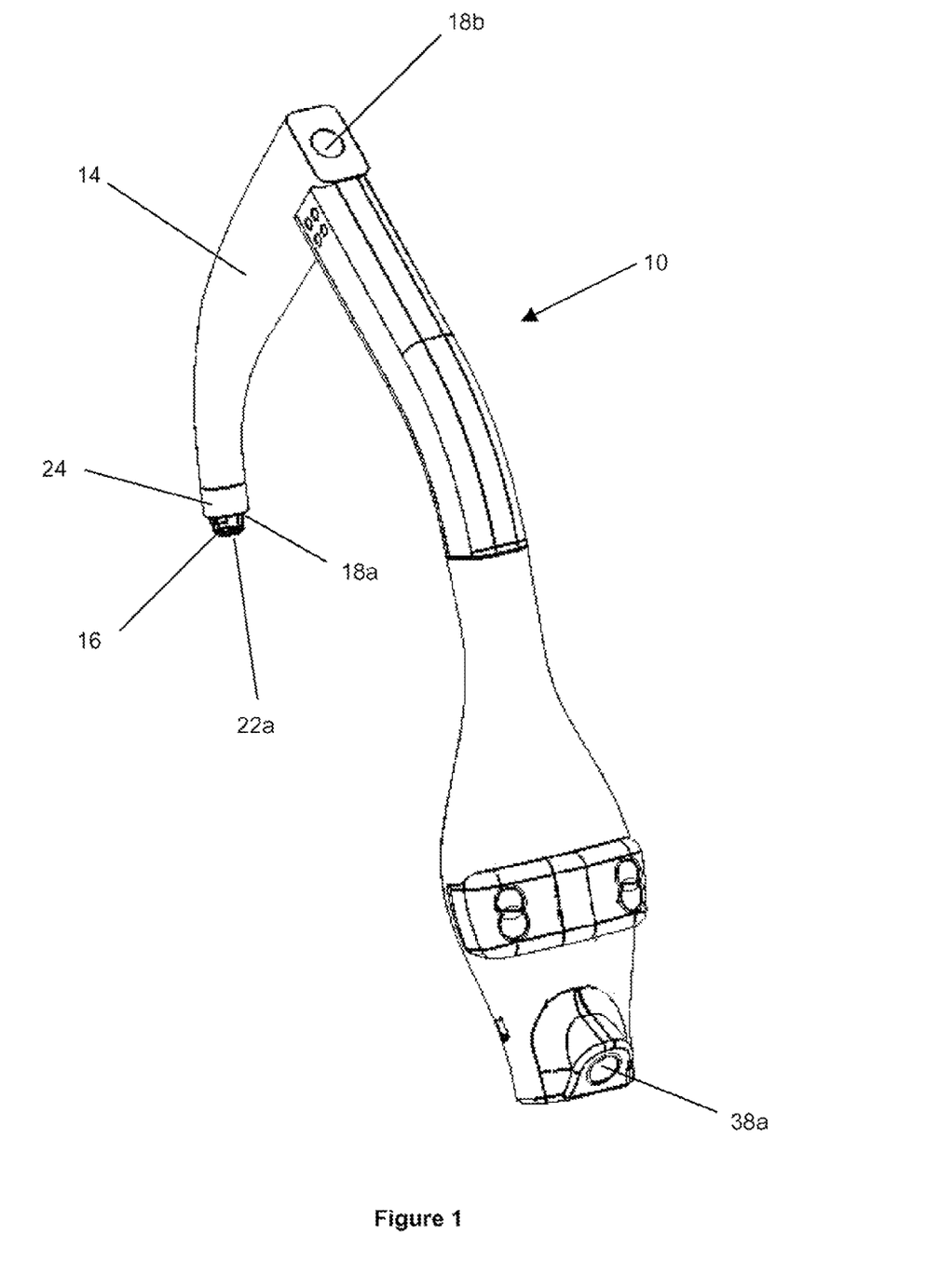
FIG. 1 is a perspective view of a jig according to a first aspect of the present invention.

Referring to FIG. 1, there is provided a jig 10 according to a first aspect of the present invention. The jig 10 comprises a guide 14 and a connecting element 16. The jig 10 is intended for use in connection with a bone fixation device 12 (see FIG. 2), which device can be a bone fixation rod (or nail). In a preferred embodiment, the bone fixation device 12 is an intramedullary rod (or intramedullary nail), but it will be clearly seen that the jig 10 is suitable for use in connection with any similar bone fixation device, which can be selected by one skilled in the art.

The guide 14 defines a non-rectilinear path. In a preferred embodiment, at least part of the guide 14 defines a non-rectilinear path. Optionally, at least part of the guide 14 defines a curvilinear path. The curvilinear path defined by the guide 14 allows the user to access a bone fixation device 12 and to reversibly engage the jig 10 with the bone fixation device 12 from a location remote from the bone fixation device 12. Each of the ends 18a, 18b of the guide 14 do not share the same rectilinear axis, which allows the user to access the bone fixation device 12 from a location, which does not share the same rectilinear axis as the bone fixation device 12. Advantageously, in the case of an intramedullary nail 12, the user can access the intramedullary nail 12 from a location, which is not obscured by at least part of a patient. Specifically, a user can access the intramedullary nail 12 from a location, which is not obscured by the tissues flanking the medullary canal of a bone. In a preferred embodiment, the first 18a end of the guide 14 is in non-parallel orientation with respect to the second 18b end of the guide 14, defining an internal angle of between 45 and 90°. However, it will be understood that any internal angle, which provides a guide 14, wherein each of the ends 18a, 18b of the guide 14 do not share the same rectilinear axis would also fulfil the object of the present invention.

The guide 14 is adapted to receive the connecting element 16, and is adapted to allow the passage of the connecting element 16 therethrough. In a preferred embodiment, the guide 14 has a hollow cylindrical body having first 18a and second 18b open ends. In use, the connecting element 16 is located adjacent a first end 18a of the guide 14 for reversible engagement with a bone fixation device 12. In a preferred embodiment, the connecting element 16 is introduced at the second 18b end of the guide 14 and can pass through the guide 14 to the first 18a end of the guide 14.

The connecting element 16 is adapted for remote reversible engagement with the bone fixation device 12. Preferably, the connecting element 16 is arranged for rotational movement relative to the guide 14. In a preferred embodiment, the connecting element 16 has a hollow cylindrical body, and is shaped and dimensioned for co-axial rotational movement within the guide 14, and about a longitudinal axis of the guide 14.

Figure 2:
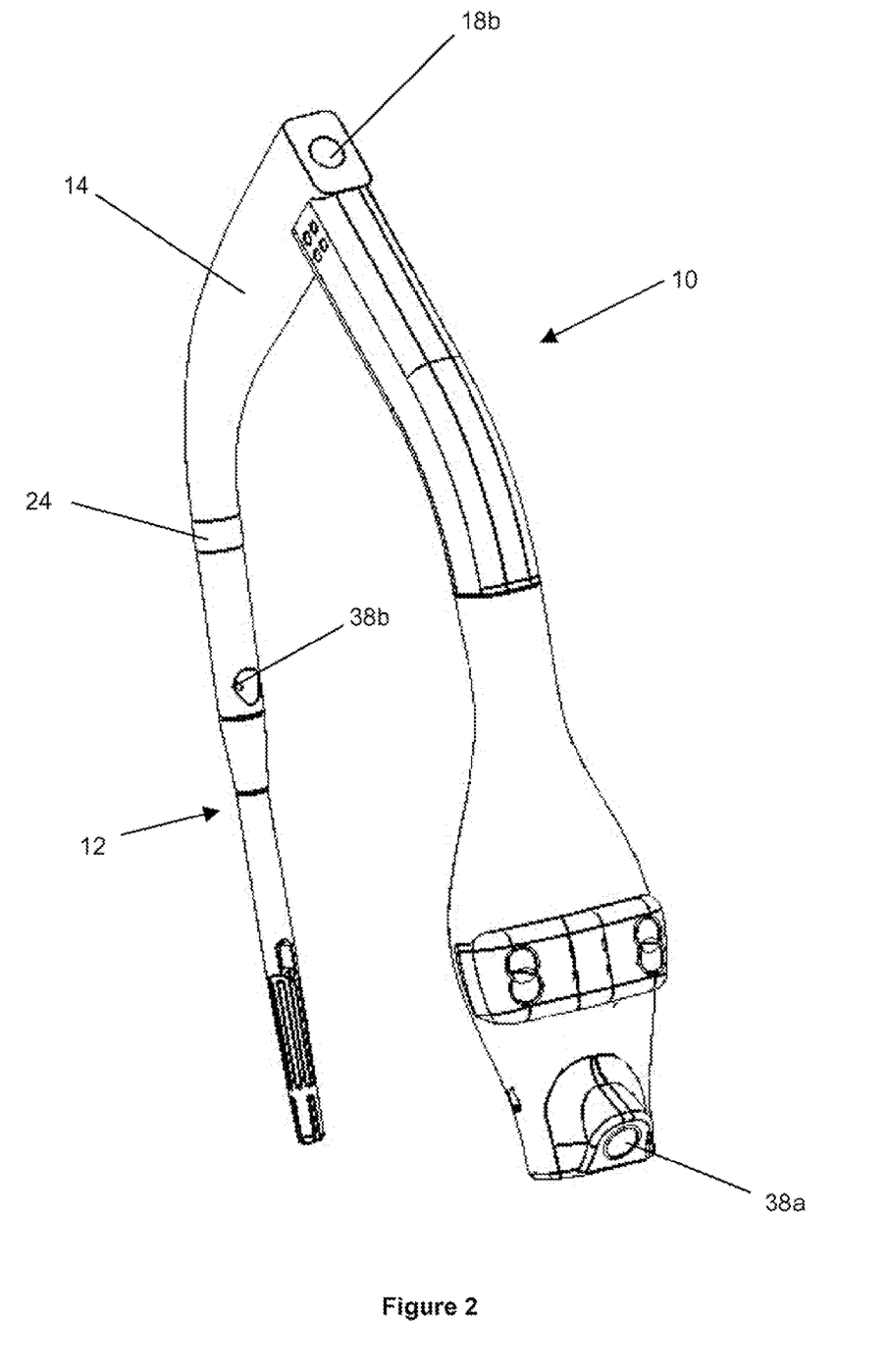
FIG. 2 is a perspective view of the jig of FIG. 1 engaged with a bone fixation device.
Figure 3:
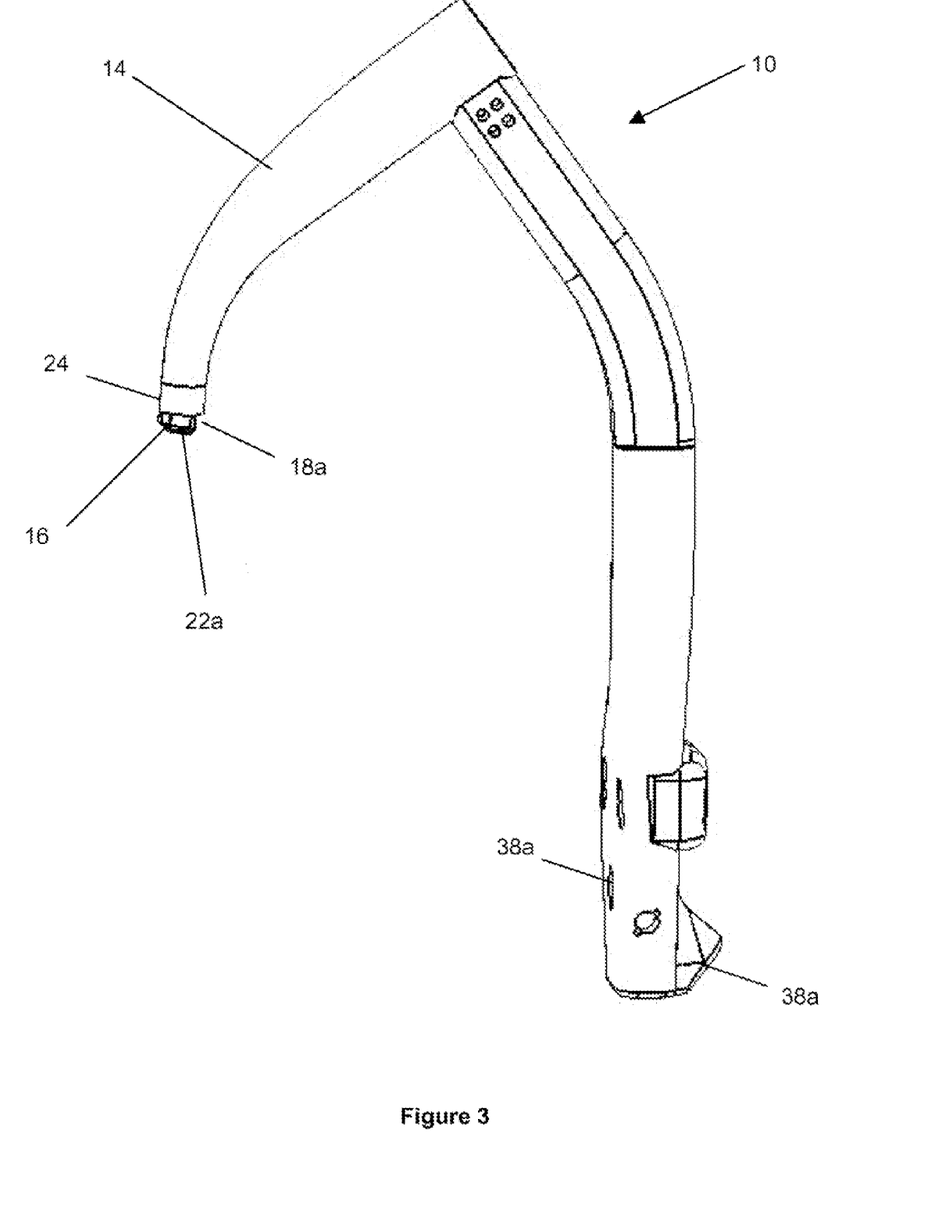
FIG. 3 is a side view of the jig of FIG. 1.
Figure 4:
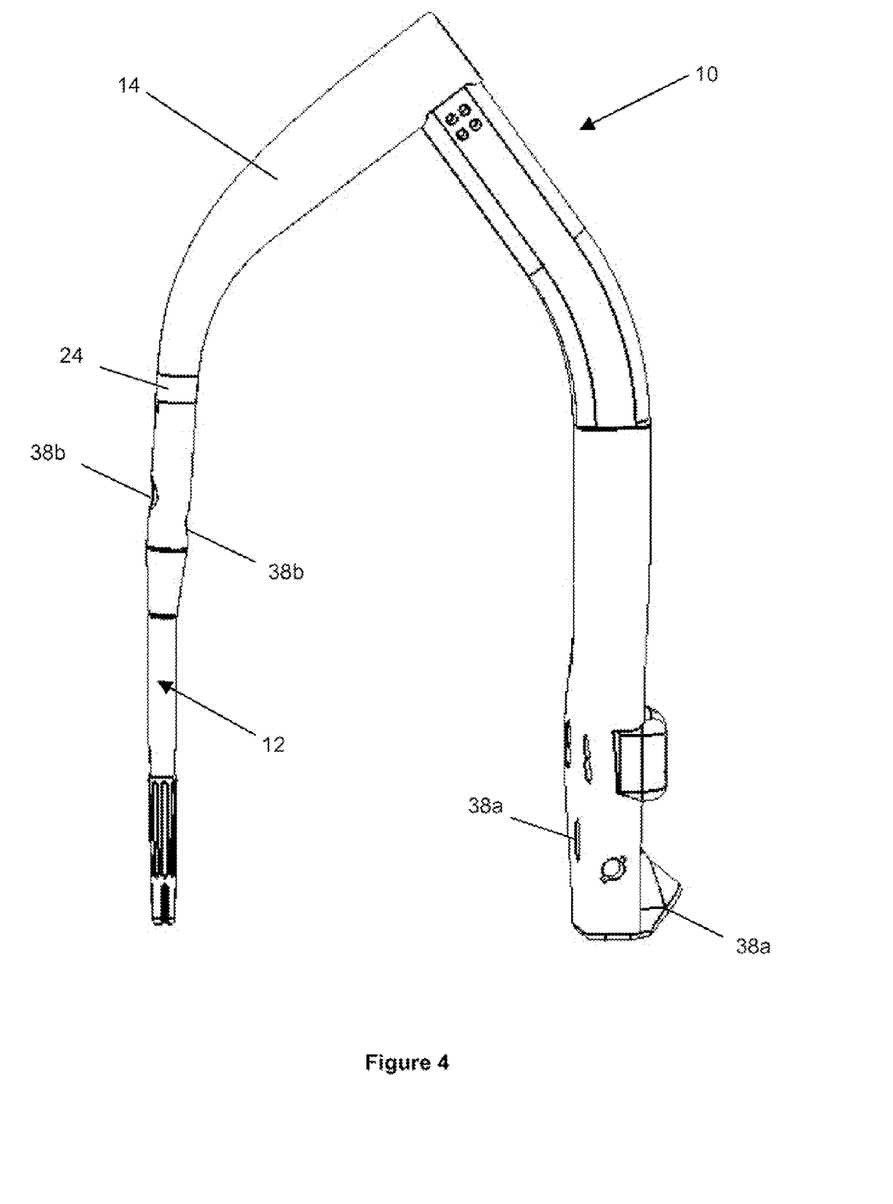
FIG. 4 is a side view of the jig of FIG. 2.
Figure 5:
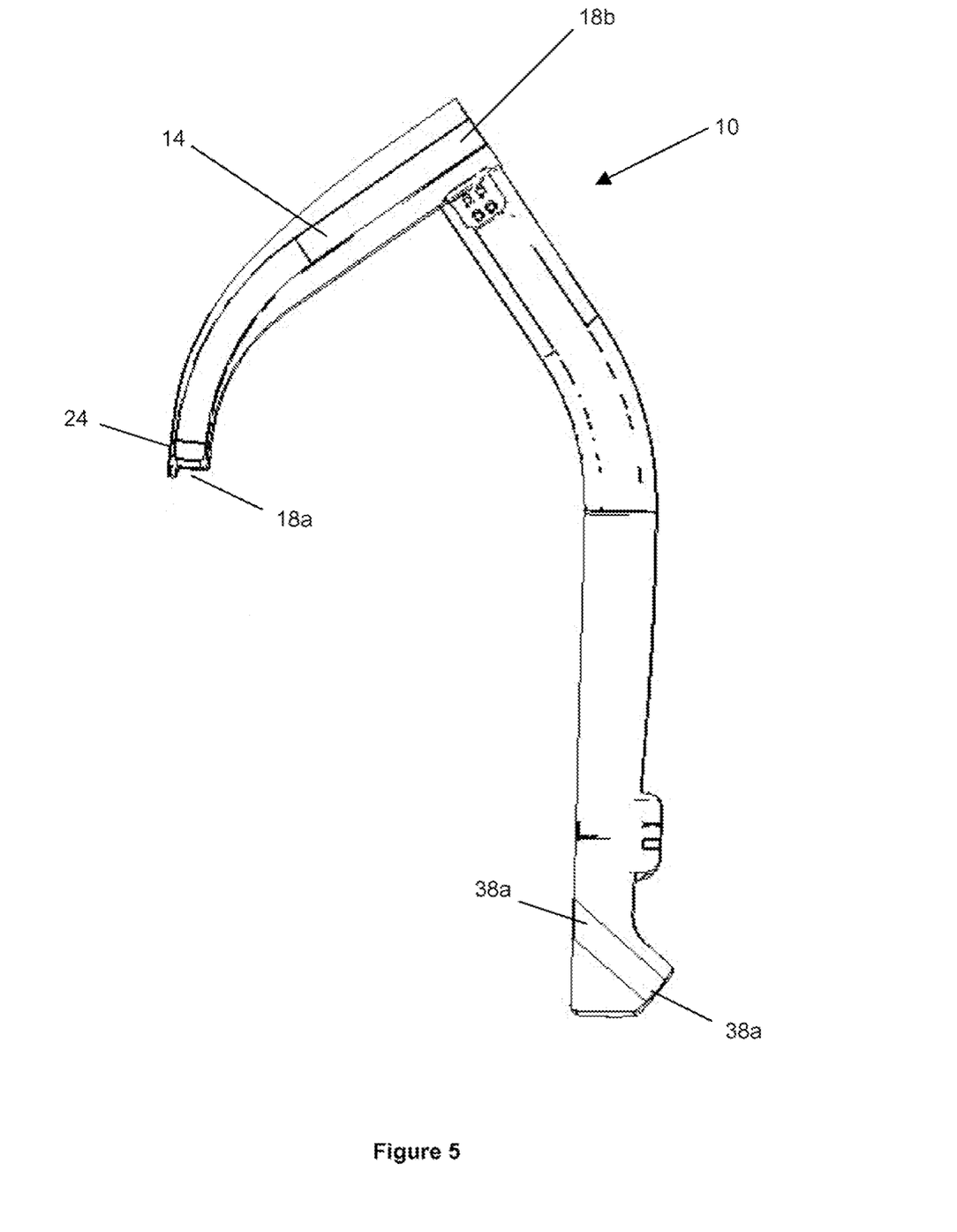
FIG. 5 is a sectional side view of the jig of FIG. 1.
Figure 6:
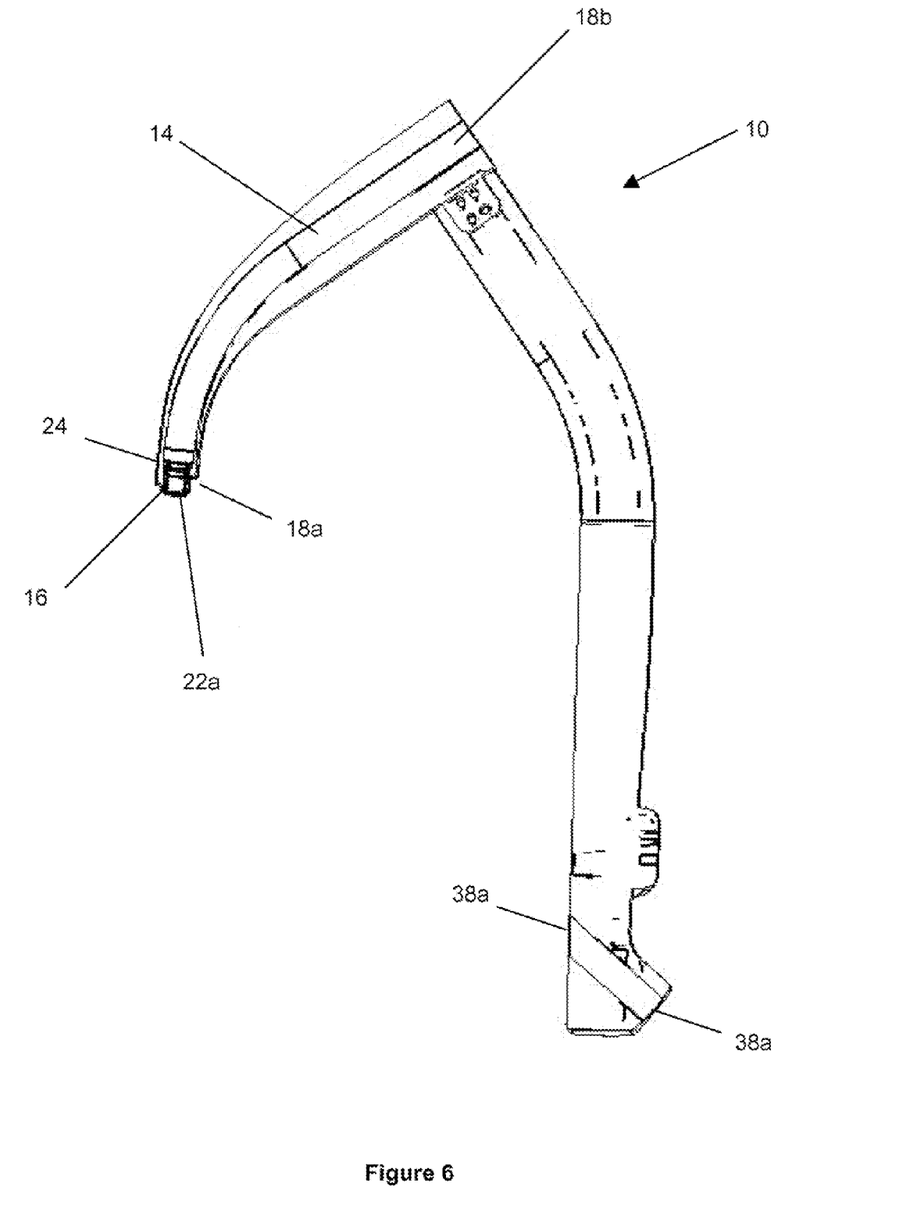
FIG. 6 is a sectional side view of the jig of FIG. 1 and a connecting element.
Figure 7:
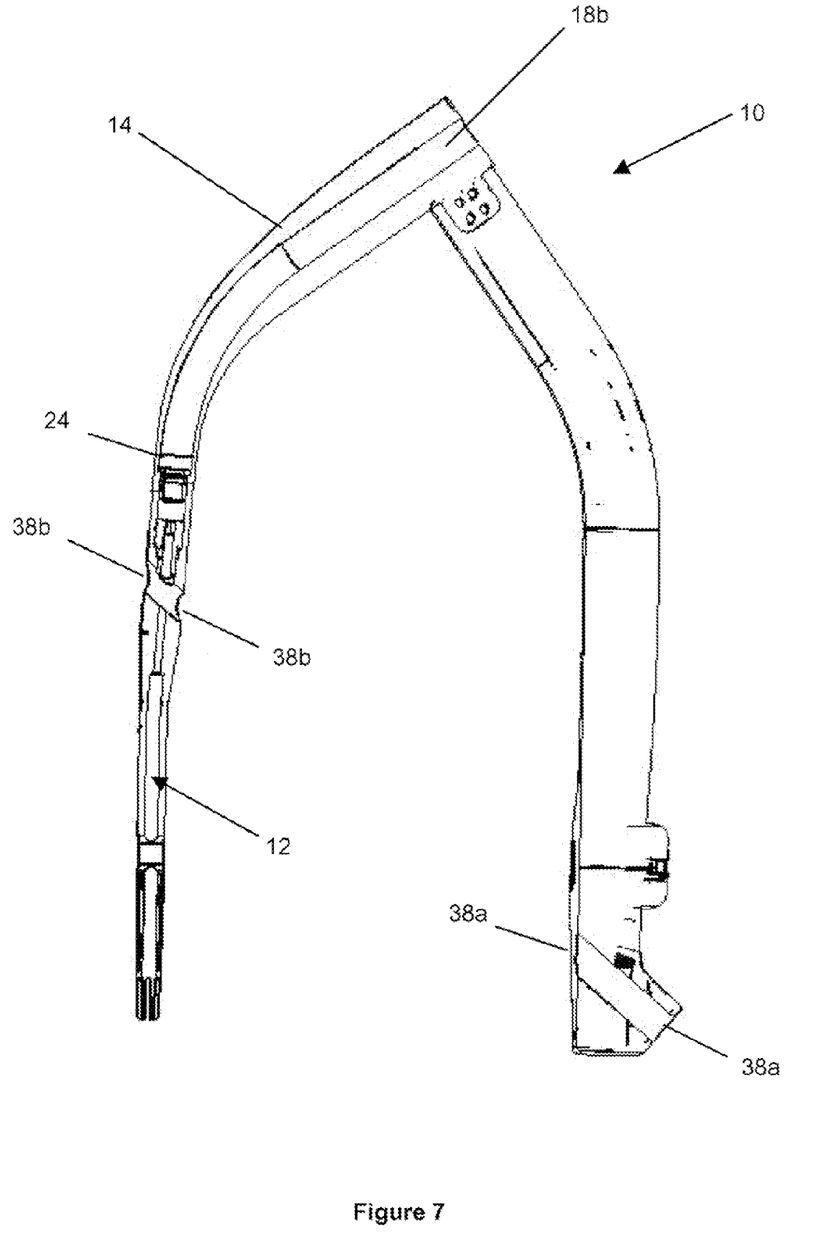
FIG. 7 is a sectional side view of the jig of FIG. 2.

The connecting element 16 is adapted to reversibly engage the bone fixation device 12. In a preferred embodiment, the connecting element 16 is adapted for threaded engagement with the bone fixation device 12. The connecting element 16 comprises a screw thread 22a for threaded engagement with a corresponding screw thread 22b of the bone fixation device 12. The screw thread 22a is located at a bone fixation device-engaging face of the connecting element 16, and the corresponding screw thread 22b is located at a connecting element-engaging face of the bone fixation device 12. In an alternative embodiment, the connecting element 16 is shaped and dimensioned to form an interference fit with the bone fixation device 12.

In a preferred embodiment, the connecting element 16 comprises a nut, which is adapted to allow the passage of a tool (not shown) therethrough. Optionally, the connecting element 16 comprises a nut having an aperture to allow the passage of a tool (not shown) therethrough. The connecting element 16 may be integral with the guide 14 but, in a preferred embodiment, the connecting element 16 is separate from the guide 14, and the guide 14 is adapted to receive the connecting element 16 at the second end 18b of the guide 14 and to allow the passage of the connecting element 16 through the guide 14 to the first end 18a. The guide 14 preferably comprises a stop 24 to reversibly retain the connecting element 16 adjacent or at the first end 18a of the guide 14. The stop 24 comprises a projection, which projects radially inward with respect to the first end 18a of the guide 14 to reversibly retain the connecting element at the first end 18a of the guide. The projection defines an aperture, which permits the passage of a tool (not shown) therethrough.

Figure 8A:
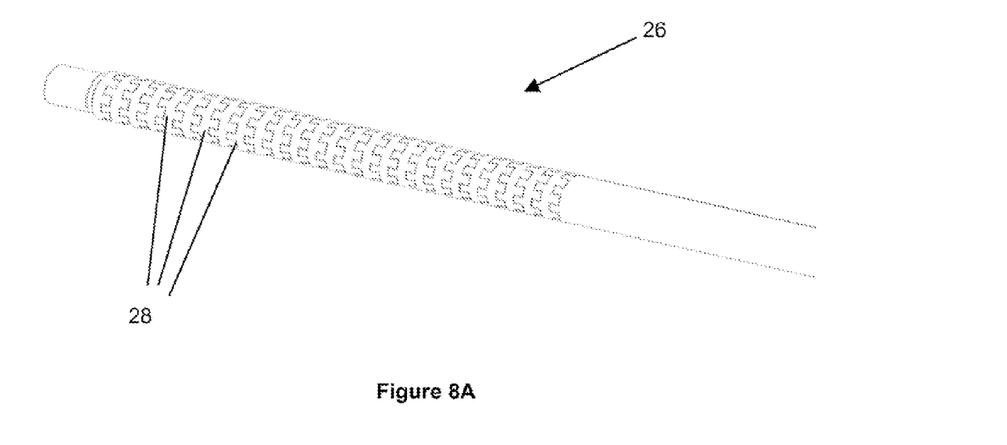
FIG. 8A is a perspective view of an actuator of the jig according to a first aspect of the present invention, wherein the segments are in side-by-side relationship.
Figure 8B:
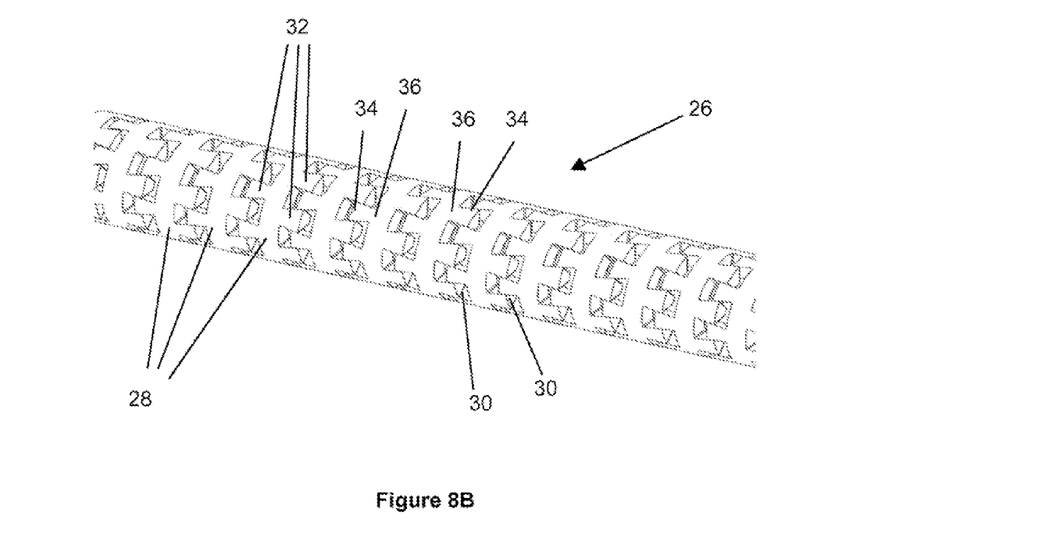
FIG. 8B is a perspective view of the actuator of FIG. 8A, wherein the segments are in spaced apart relationship.

Referring to FIG. 8, the connecting element comprises an actuator 26, which is arranged for rotational motion relative to the guide 14. In a preferred embodiment, the actuator 26 is integral with the connecting means 16, wherein the connecting means 16 is located at a terminal end of the actuator 26.

In an alternative embodiment, the actuator 26 is separate from the connecting means 16, and is adapted to reversibly engage the connecting element 16. The actuator 26 may be shaped and dimensioned to reversibly engage the connecting element 16, for example, by way of an interference fit. Alternatively or additionally, the actuator may reversibly engage the connecting element by way of a reversible coupling, such as a magnetic coupling.

In a preferred embodiment, the actuator 26 comprises a hollow cylindrical body, which can extend between the first 18a and second 18b ends of the guide 14. In use, the actuator 26 is co-axial with, and extends between, the first 18a and second 18b ends of the guide 14. Advantageously, the actuator 26 is arranged for coaxial rotation relative to the guide 14, and about a longitudinal axis of the guide 14. In such an arrangement, the actuator 26 is arranged to permit rotation of the connecting means 16 at the first end 18a of the guide 14. In use, the actuator 26 is arranged to permit rotation of the connecting means at the first end 18a of the guide 14 by rotation of the actuator 26 at the second end of the guide 14, such that the actuator 26 translates rotational motion of the actuator at the second end 18b of the guide 14 to rotational motion of the connecting means 16 at the first end 18a of the guide 14. Given the non-rectilinear path defined by the guide 14, the actuator 26 is capable of translating rotational motion of the actuator 26 at the second end 18b of the guide 14 in a first plane to rotational motion of the connecting means 16 at the first end 18a of the guide 14 in a second plane, wherein the first and second planes are non-parallel planes.

In one embodiment, the actuator 26 comprises a hollow cylindrical body, which extends between the first 18a and second 18b ends of the guide 14 and is formed from a resilient material. Optionally or additionally, the actuator 26 is formed from a flexible material.

In a preferred embodiment, the actuator 26 comprises at least two segments 28, at least part of each of which is arranged for reversible displacement relative to an adjacent segment 28 of the actuator 26 with respect to the longitudinal axis of the actuator 26, such that at least part of the actuator 26 is axially deformed. In a preferred embodiment, each segment 28 is spaced apart relative to an adjacent segment 28. Optionally, each segment 28 is arranged for reversible displacement relative to an adjacent segment 28 of the actuator 26 with respect to the longitudinal axis of the actuator 26. Preferably, each segment 28 is arranged to permit limited reversible displacement relative to an adjacent segment.

Optionally, the interface of each segment 28 is crenulated, and the spaces defined between the crenels 32 (the intracrenular spaces) of each segment 28 are arranged to receive the crenels 32 of an adjacent segment 28. The crenels 32 are shaped and dimensioned to permit only limited reversible displacement between segments 28 of the actuator 26. In a preferred embodiment, the tip 34 of each crenel has a greater dimension relative to the root 36 of each crenel 32. Resultantly, the tip 34 of each crenel 32 of each segment 28 is shaped and dimensioned to, in use, engage with the root 36 of each crenel 32 of an adjacent segment 28. As can clearly be seen in FIG. 8B, the space 30 defined between two adjacent segments 28 can be adjusted longitudinally, but the segments 28 cannot be separated, thereby allowing axially deformation of the actuator 26. Advantageously, the actuator 26 is capable of rotational movement relative to the guide 14 in first and second opposing directions without radial deformation of the actuator 26. Such an arrangement provides rotational movement in both opposing directions, without the actuator 26 deforming radially, thereby providing torque equally in both directions.

In an alternative embodiment, at least one segment 28 can be formed from a deformable material, such as rubber to allow at least part of the actuator to be axially deformed. Alternatively, the actuator 26 is in the form of a helix or coil.

In use, the guide 14 and the actuator 26 are co-axial and capable of rotational movement relative to one another. The actuator 26 is preferably adapted to allow the passage of a tool (not shown) therethrough. The tool has a flexible shaft, for example, a screwdriver having a flexible drive shaft. Advantageously, the present invention provides a jig 10, wherein, in use, the guide 14, the actuator 26, and the tool are co-axial and capable of independent rotational movement relative to one another.

The jig 10 can be formed from a sterilizable material or an autoclavable material, and is preferably formed of a material that is suitable for sterilisation, so as to be provided in a sterile packaged state for use. The material is preferably polyether ether ketone (PEEK), which is reinforced with carbon fibres. Alternatively, the material is stainless steel.

According to a second aspect of the present invention, there is provided a method for placing a bone fixation device 12 in a bone, using a jig 10 according to the first aspect of the present invention, the method comprising the step of reversibly engaging the bone fixation device 12 with the jig 10. In a preferred embodiment, the engaging step comprises engaging the connecting means 16 of the jig 10 to the bone fixation device 12. The engaging step can be achieved by rotating the connecting means 16 relative to the guide 14. Optionally, the engaging step comprises rotating the connecting means 16 by rotating the actuator 26 at the first end 18a of the guide 14 by rotating the actuator 26 at the second end 18b of the guide 14.

Once engaged, the bone fixation device 12 can be introduced into the bone. A small incision can be made adjacent, optionally proximal, to the fracture in the bone. In the case of a femur bone, the small incision can be made adjacent, optionally proximal, to the greater trochanter of the femur bone.

The bone fixation device 12 can be introduced into the medullary cavity of the bone, optionally longitudinally co-axial with the medullary cavity of the bone. To facilitate introduction of the bone fixation device 12, a channel can be provided into the medullary cavity of the bone prior to the introducing step. In the case of a femur bone, with blunt dissection, a channel can be provided to the entry point for the bone fixation device 12, the entry point being adjacent, optionally medial to, the tip of the greater trochanter of the femur bone. The channel can be provided longitudinally co-axial with, the medullary cavity of the bone prior to the introducing step. An awl, optionally a curved awl, can be used to facilitate introduction of the bone fixation device 12 by introducing a flexible guide wire, optionally a blunt-end flexible guide wire through the awl and into the medullary cavity of the bone. In a preferred embodiment, a chuck, for example, a collet can be used to advance and control the flexible guidewire. Alternatively, a drill bit can be used to provide an entry point for passing of the flexible guide wire. A reamer, optionally a conical reamer, can be used to provide the channel into the medullary cavity of the bone over the flexible guidewire. If necessary, further reaming of the medullary cavity of the bone may then be performed using flexible reamers, firstly, for example, using a 9.0 mm flexible reamer and increasing in sequential 1.0 mm increments. If using a long bone fixation device 12, the channel provided in the medullary cavity of the bone should be, for example, 2.0 mm greater than the outer diameter of the bone fixation device 12.

The bone fixation device 12 is introduced over the flexible guidewire into the channel provided in the medullary cavity of the bone. In extreme cases, if a mallet is required to advance the bone fixation device 12, gentle hits with the mallet are permitted at the second end 18b of the guide 14. The flexible guidewire can be removed following placement of the bone fixation device 12.

The present invention also relates to a method for the fixation of a bone having a fracture. Following the method for placing the bone fixation device 12 in the bone using the jig 10 according to the first aspect of the present invention, the method further comprises the step of fixing a fracture in the bone. The fixing step can comprise providing a channel across the fracture in the bone.

The channel can extend between the at least one drill guide of the jig 38a and the respective at least one drill guide of the bone fixation device 38b.

In a preferred embodiment, the fixing step further comprises introducing a fracture-fixing device across the fracture in the bone; which can be facilitated by introducing the fracture-fixing device into the channel extending between the at least one drill guide of the jig 38a and the respective at least one drill guide of the bone fixation device 38b. Adjustment of the depth and rotation of the bone fixation device 12 may be necessary to achieve optimal 'centre-centre' placement on both antero-posterior and lateral views, with a combined tip-apex distance of, for example, less than 25 mm in the case of a femur bone.

Once the fracture-fixing device is introduced across the fracture in the bone, the fracture-fixing device can be engaged with the bone fixation device 12. In a preferred embodiment, the fixing step further comprises engaging the fracture-fixing device with the bone fixation device 12 using a tool by rotating a screw (not shown) located, in use, adjacent the drill guide 38b of the bone fixation device using the tool.

Following engagement of the fracture-fixing device with the bone fixation device, the connecting means 16 of the jig 10 can be disengaged from the bone fixation device 12. Preferably, the disengaging step comprises rotating the connecting means 16 relative to the guide 14. The disengaging step can comprises rotating the connecting means 16 by rotating the actuator 26 in the direction opposite to the engaging step. Further optionally, the disengaging step comprises rotating the connecting means 16 at the first end of the guide 18a by rotating the actuator 26 at the second end of the guide 18b in the direction opposite to the engaging step.

Should an end cap to the bone fixation device 12 be required, the flexible guidewire is re-inserted into the top of the bone fixation device 12; and an appropriately sized end cap is inserted using the tool over the guidewire; and then guidewire is removed.

The method can further comprise the step of reducing the fracture, prior to the providing step. Traction and rotation are each applied to the bone to achieve a reduction of the fracture. The fracture can be reduced by closed methods, without surgical exposure of the fracture. If an anatomical reduction is not possible by closed means, the fracture can be reduced by percutaneous methods, with partial surgical exposure of the fracture. If necessary, the fracture can be reduced by open methods, with surgical exposure of the fracture.

Optionally, the method is conducted in connection with fluoroscopic techniques. Further optionally, the method is conducted in connection with image-intensifier fluoroscopic techniques. Still further optionally, the method is conducted in connection with x-ray image-intensifier fluoroscopic techniques. Alternatively, the method is conducted in connection with gamma-ray image-intensifier fluoroscopic techniques.

The method can be conducted on a patient oriented in the supine position; or, alternatively, the method can be conducted on a patient oriented in the lateral decubitous position, optionally with traction and rotation of the bone being provided by an assistant; which can counteract deforming muscle forces from preventing fracture reduction, particularly in subtrochanteric fractures, and may facilitate the surgical view if performing an open reduction of the fracture.

The invention is not limited to the embodiments described herein but can be amended or modified without departing from the scope of the present invention.

We claim:

1. A jig for a bone fixation device, the jig comprising a guide; and a connecting element reversibly engagable with the bone fixation device; wherein the guide defines a non-rectilinear path and has a hollow cylindrical body and first and second open ends to allow the passage of the connecting element therethrough; and wherein the first end of the guide is in non-parallel orientation with respect to the second end of the guide; and wherein the connecting element is remotely operable, and is adapted to permit a tool to be engaged with the bone fixation device; and wherein the connecting element comprises an actuator arranged for rotational motion relative to the guide; and wherein the actuator comprises a hollow cylindrical body, which is, in use, co-axial with, and extends between the first and second ends of, the guide and wherein the actuator comprises at least two segments, which are each arranged for reciprocal movement relative to the other segment with respect to the longitudinal axis of the actuator, and wherein each segment is crenulated and comprises crenels arranged to receive crenels of an adjacent segment.

2. A jig according to claim 1, wherein the connecting element is adapted for threaded engagement with the bone fixation device.

3. A jig according to claim 1, wherein the connecting element comprises an aperture to allow the passage of a tool therethrough.

4. A jig according to claim 1, wherein the actuator is arranged to permit rotation of the connecting means at the first end of the guide by rotation of the actuator at the second end of the guide.

5. A jig according to claim 1, wherein at least part of each segment of the actuator is arranged for reversible displacement relative to an adjacent segment of the actuator with respect to the longitudinal axis of the actuator.

6. A jig according to claim 1, wherein each segment is arranged for limited reversible displacement relative to an adjacent segment of the actuator with respect to the longitudinal axis of the actuator.

7. A jig according to claim 1, wherein the crenels of each segment are arranged for limited reversible displacement relative to the crenels of an adjacent segment of the actuator with respect to the longitudinal axis of the actuator.

8. A jig according to claim 7, wherein the tip of each crenel has a greater dimension relative to the root of each crenel.

9. A jig according to claim 1, wherein, in use, the guide, the actuator, and the tool are co-axial and capable of independent rotational movement relative to one another.

10. A jig according to claim 1, wherein the bone fixation device further comprises a device to fix a fracture in the bone, and wherein the bone fixation device is adapted to be reversibly engagable with the fracture-fixing device.

11. A method for placing a bone fixation device in a bone, using a jig according to claim 1, the method comprising the step of reversibly engaging the bone fixation device with the jig.

12. A method according to claim 11, wherein the engaging step further comprises rotating the connecting means at the first end of the guide by rotating the actuator at the second end of the guide.

13. A method according to claim 12, wherein the engaging step comprises passing the actuator through the guide such that the guide and the actuator are co-axial and capable of rotational movement relative to one another.

14. A method according to claim 11, wherein the method further comprises the step of introducing the bone fixation device into the bone.

15. A method according to claim 11, wherein the method further comprises the step of fixing a fracture in the bone, the fixing step comprising introducing a fracture-fixing device across the fracture in the bone.

16. A method according to claim 15, wherein the fixing step further comprises engaging the fracture-fixing device with the bone fixation device.

17. A method according to claim 15, wherein the fixing step comprises passing the tool through the actuator such that the tool and the actuator are co-axial and capable of rotational movement relative to one another.

18. A method according to claim 15, wherein the fixing step comprises passing the tool through the actuator such that the tool and the actuator and the guide are co-axial and capable of independent rotational movement relative to one another.

\* \* \* \* \*